US00PP21037P3

(12) United States Plant Patent
Nielsen

(10) Patent No.: US PP21,037 P3
(45) Date of Patent: Jun. 1, 2010

(54) *DAHLIA* PLANT NAMED 'DASYTTEN'

(50) Latin Name: *Dahlia sp.*
Varietal Denomination: DASTYTTEN

(75) Inventor: Rune Harboe Nielsen, Odense (DK)

(73) Assignee: Dalina APS, Odense N (DK)

( * ) Notice: Subject to any disclaimer, the term of this patent is extended or adjusted under 35 U.S.C. 154(b) by 0 days.

(21) Appl. No.: 12/381,691

(22) Filed: Mar. 16, 2009

(65) Prior Publication Data

US 2009/0235418 P1 Sep. 17, 2009

(30) Foreign Application Priority Data

Mar. 17, 2008 (QZ) ..... PBR 2008/0600

(51) Int. Cl.
*A01H 5/00* (2006.01)

(52) U.S. Cl. ..... Plt./321

(58) Field of Classification Search ..... Plt./321
See application file for complete search history.

*Primary Examiner*—Annette H Para
(74) *Attorney, Agent, or Firm*—Foley & Lardner LLP

(57) ABSTRACT

A new and distinct cultivar of *Dahlia* plant named 'DASYTTEN' characterized by ray floret color (fully opened): upper side: near base, green-yellow, RHS 1B transitioning to yellow-orange, RHS 17C; capitulum (composite flower head): 8 cm in diameter, with a large number of ray florets (about 110 to 140); foliage: mature leaves are up to 7 cm in length, mostly compound, with 3 to 5 elliptic leaflets; and plant vigor and growth habit: vigorous, grows upright and is cylindrical in shape.

5 Drawing Sheets

Latin name of the genus and species of the claimed plant: *Dahlia* sp.

Variety denomination: 'DASYTTEN'.

BACKGROUND OF THE INVENTION

The present invention relates to a new and distinct cultivar of *Dahlia* plant, botanically known as *Dahlia* sp. of the Compositae (Asteraceae) family, hereinafter referred to by the cultivar name 'DASYTTEN'.

The new *Dahlia* cultivar is a product of a planned breeding program conducted by the inventor, Rune Harboe Nielsen, in Fyn, Denmark. The objective of the breeding program is to develop a new *Dahlia* variety with an upright, strong and healthy growth habit, suitable for large scale container production; fully double flowers creating globular-shaped flower head (composite flower heads with many ray florets).

The new *Dahlia* cultivar originated from a cross made in a controlled breeding program by the inventor in 2004 in Fyn, Odense, Denmark. The female or seed parent is the *Dahlia* Cav. designated '01.1076F Toluca' (unpatented). The male or pollen parent is the *Dahlia hortensis* Guillaumin designated '03.1181N' (unpatented). The new *Dahlia* 'DASYTTEN' was discovered and selected by the inventor as a single flowering plant within the progeny of the stated cross in July of 2004 in a controlled environment in Fyn, Denmark.

Asexual reproduction of the new *Dahlia* cultivar by vegetative cuttings was first performed in February of 2005 in Fyn, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DASYTTEN', which in combination distinguish this *Dahlia* as a new and distinct cultivar:

1. Ray floret color (fully opened): upper side: near base, green-yellow, RHS 1B transitioning to yellow-orange, RHS 17C;
2. Capitulum (composite flower head): 8 cm in diameter, with a large number of ray florets (about 110 to 140);
3. Foliage: Mature leaves are up to 7 cm in length, mostly compound, with 3 to 5 elliptic leaflets; and
4. Plant Vigor and Growth Habit: Vigorous, grows upright and is cylindrical in shape.

Plants of the new *Dahlia* 'DASYTTEN' differ from the parental plants, *Dahlia* Cav. designated '01.1076F Toluca' and *Dahlia hortensis* Guillaumin designated '03.1181N' (unpatented), in the characteristics described in Table 1.

TABLE 1

| Characteristic | New Cultivar 'DASYTTEN' | Female Parent '01.1076F Toluca' (unpatented) | Male Parent '03-1181N' (unpatented) |
|---|---|---|---|
| Flower Color | Yellow-green to yellow-orange | Yellow to yellow-orange | Orange |
| Capitulum Diameter: | About 10 cm | About 11 cm | About 7.5 cm |
| Mature Leaf Length: | Up to 8 cm | About 12 cm | About 8 cm |
| Plant Vigor: | Vigorous | Vigorous | Moderately vigorous |
| Plant Height: | About 47 cm | About 42 cm | About 18 cm |
| Plant Diameter: | About 37 cm | About 40 cm | About 20 cm |

Of the many commercial cultivars known to the present inventor, the most similar in comparison to the new *Dahlia* 'DASYTTEN' are the *Dahlia* sp. 'DAFEMTEN' (patented, U.S. Plant Pat. No. 19,185) and *Dahlia* sp. 'DA12' (patented, U.S. Plant Pat. No. 19,632) in the characteristics described in Table 2:

TABLE 2

| Characteristic | New Cultivar 'DASYTTEN' | Comparison 'DAFEMTEN' (patented, U.S. Plant Pat. No. 19,185) | Comparison Dahlia sp. 'DA12' (patented, U.S. Plant Pat. No. 19,632) |
|---|---|---|---|
| Mature Ray Floret Color (upper surface): | Yellow to Orange-Red | Yellow-orange | Red |
| Capitulum Diameter: | About 8.5 cm | About 8 cm | About 10.25 cm |
| Mature Leaf Length: | Up to 12 cm | About 4 to 7 cm | About 6 to 15 cm |
| Plant Vigor: | Moderately vigorous | Vigorous | Vigorous |
| Plant Height: | About 14.5 cm | About 16.5 cm | About 42.5 cm |
| Plant Diameter: | About 17.5 cm | About 19 cm | About 40 cm |

BRIEF DESCRIPTION OF THE PHOTOGRAPHS

The accompanying photographs illustrate the overall appearance of the new *Dahlia* 'DASYTTEN' showing the colors as true as is reasonably possible with colored reproductions of this type. Colors in the photographs may differ slightly from the color value cited in the detailed botanical description which accurately describes the color of 'DASYTTEN'.

DETAILED BOTANICAL DESCRIPTION

Figure 1:
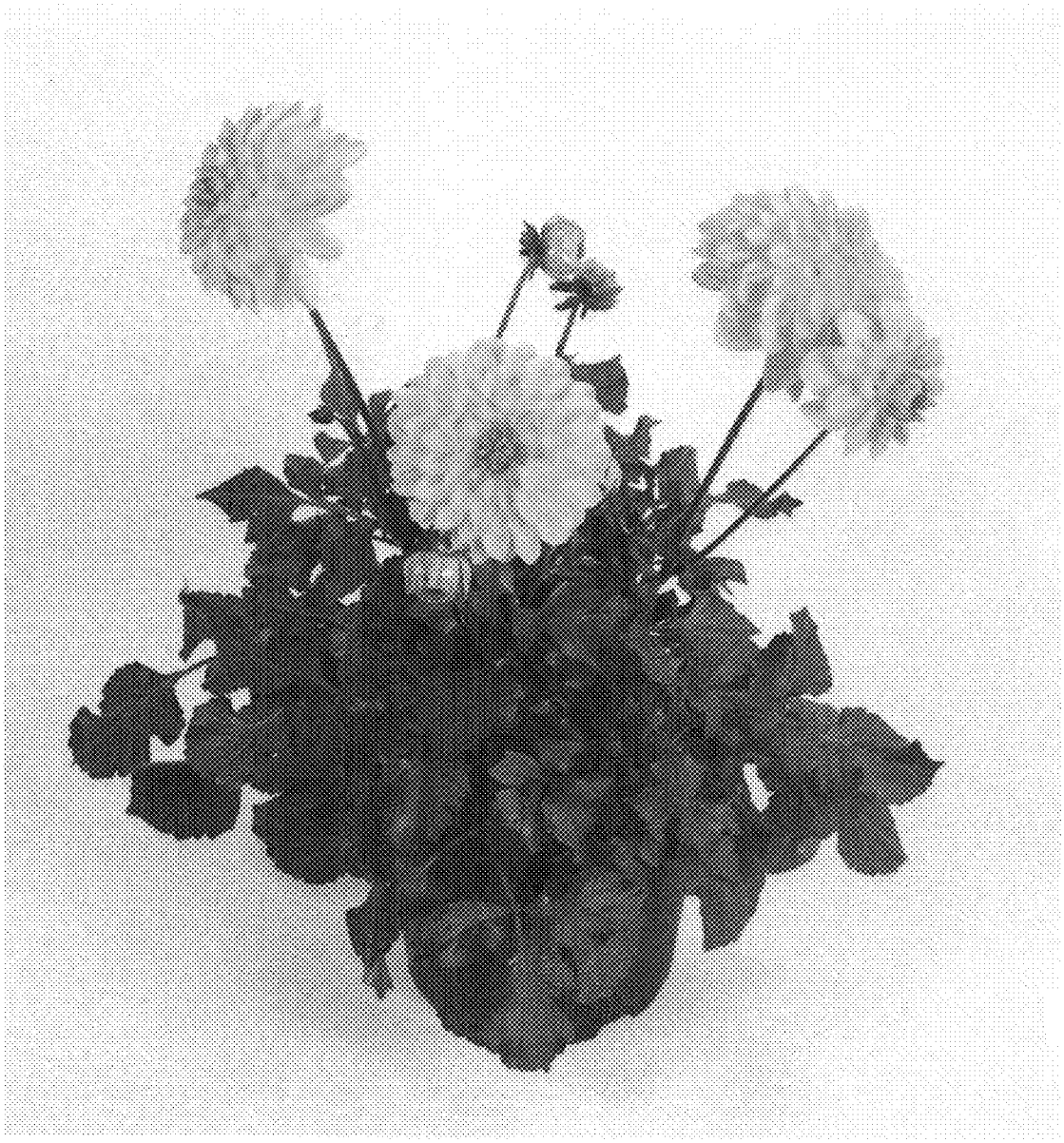
FIG. 1 shows a side view perspective of a typical flowering plant of 'DASYTTEN' in a 11 cm pot, at 13 weeks of age after planting.
Figure 2:
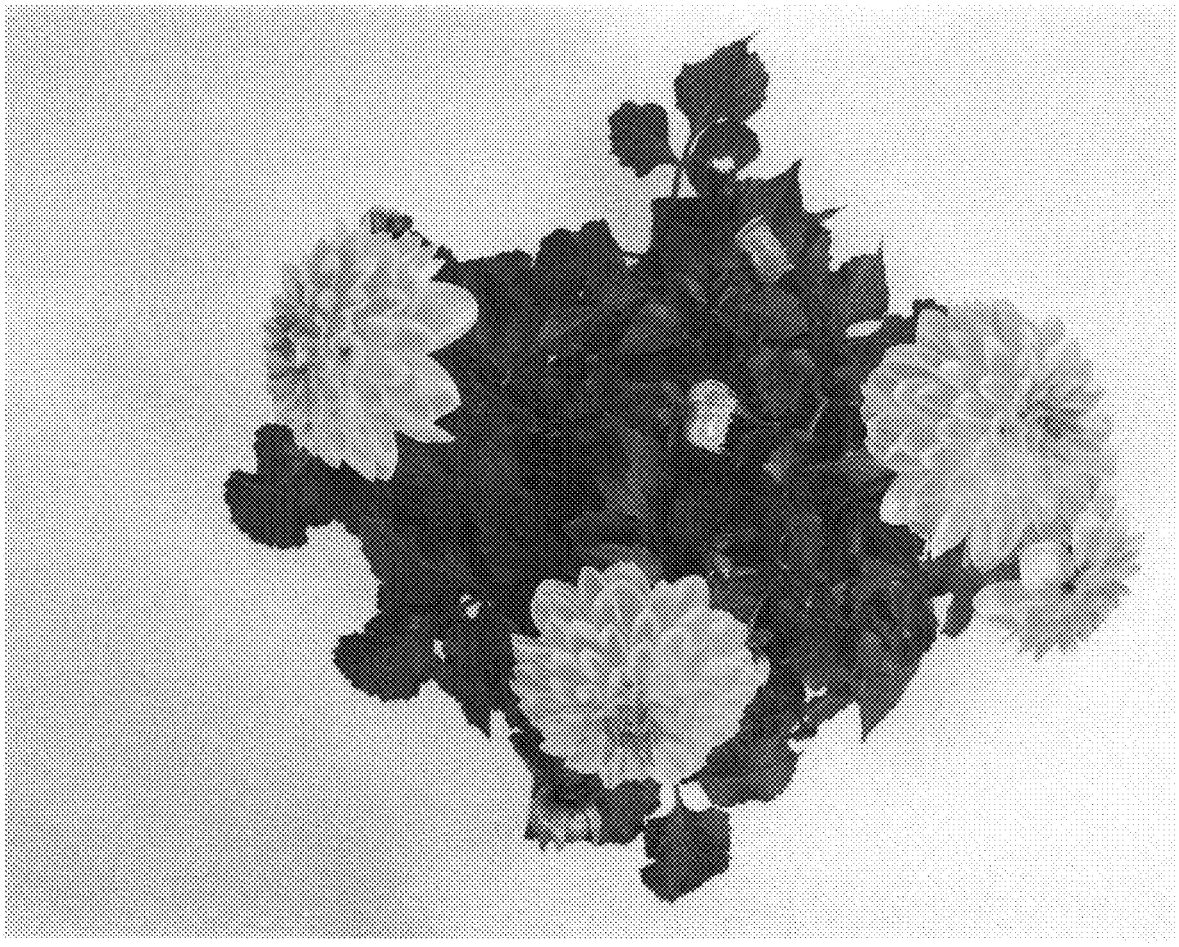
FIG. 2 shows a top view perspective of a typical flowering plant of 'DASYTTEN' in a 11 cm pot, at 13 weeks of age after planting.
Figure 3:
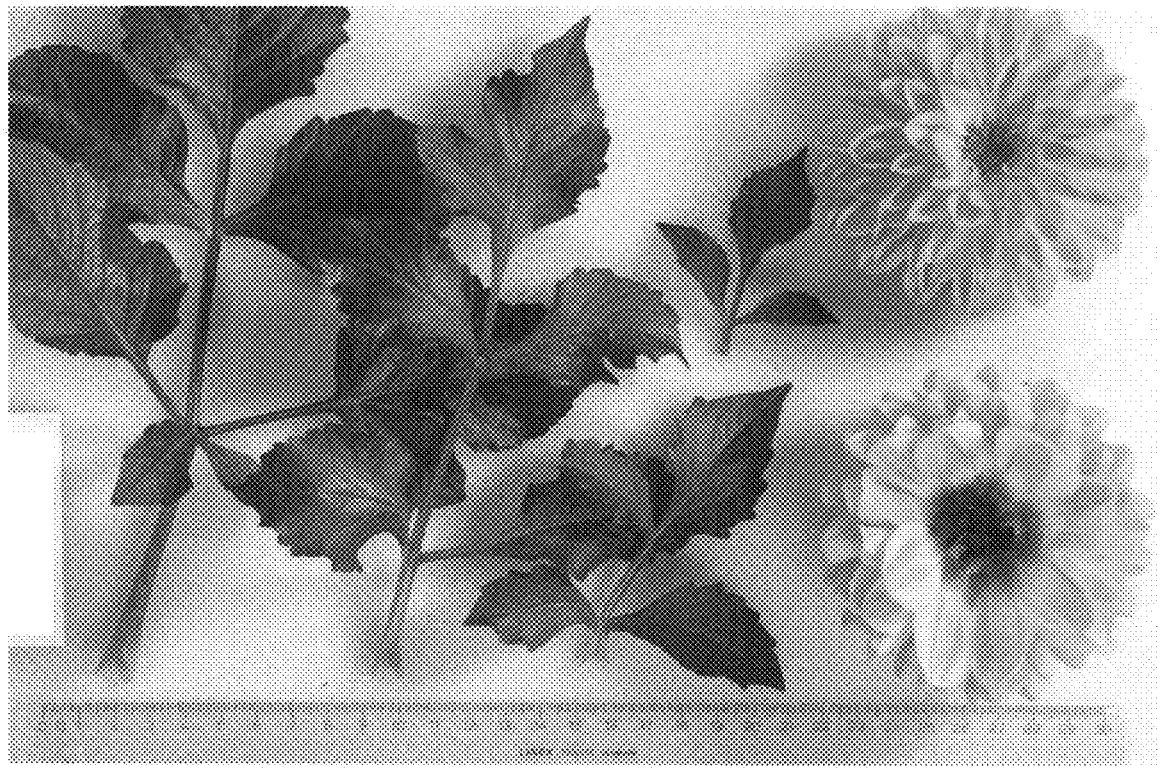
FIG. 3 shows a close-up top view of the typical foliage, as well as, a top and bottom view of a fully opened capitulum of 'DASYTTEN', at 13 weeks of age after planting.
Figure 4:
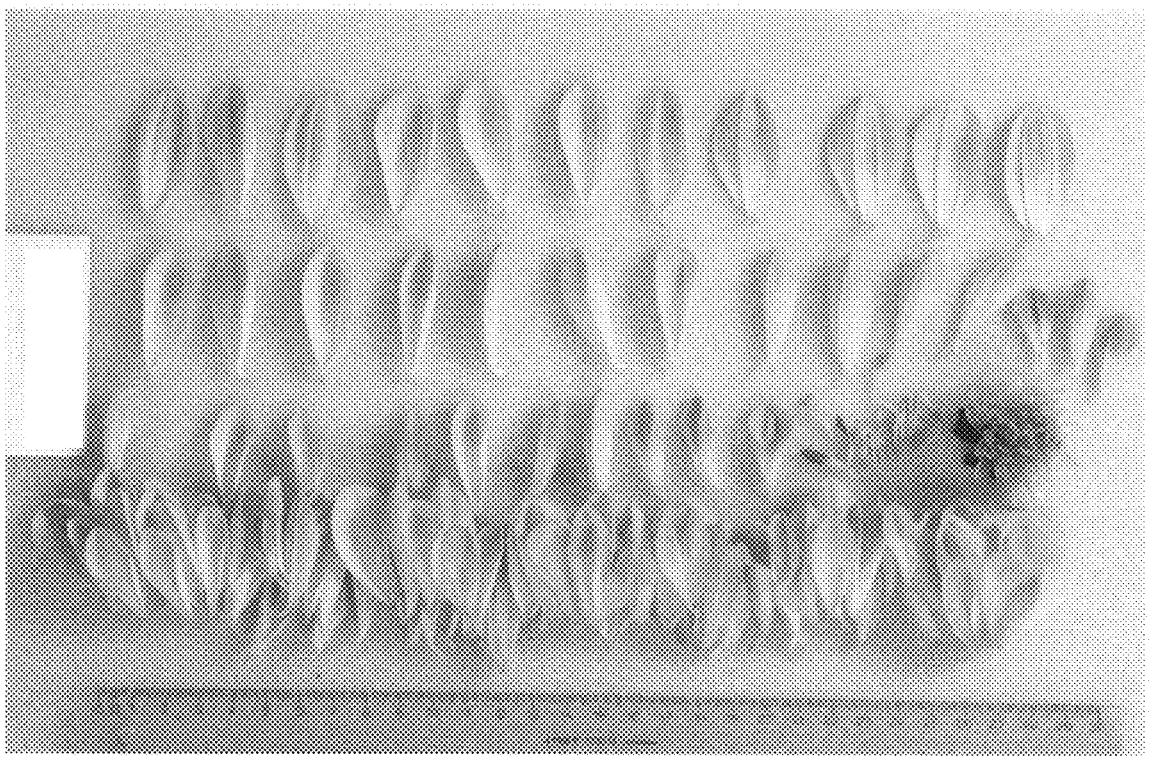
FIG. 4 shows a close-up view of the detailed floral parts of a fully opened capitulum of 'DASYTTEN'.
Figure 5:
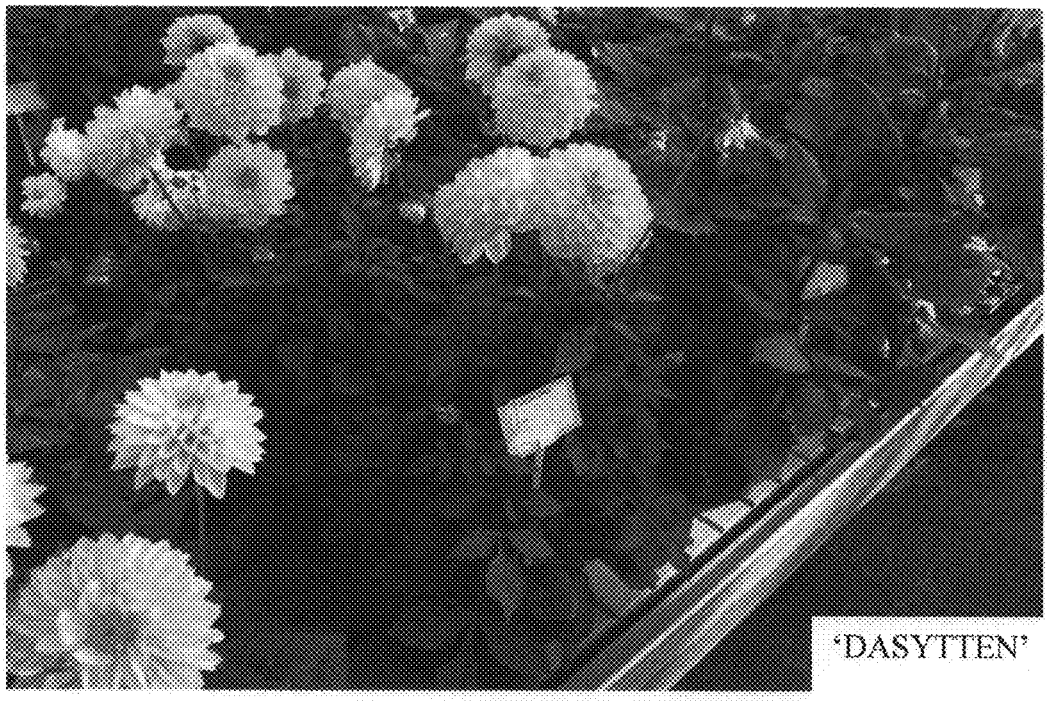
FIG. 5 shows a comparison view of a typical mature flowering plant of the new cultivar 'DASYTTEN' (top) in a 11 cm pot compared to a typical mature flowering plant of the comparison cultivar 'DAFEMTEN' in a 11 cm pot (bottom).
Figure 5:
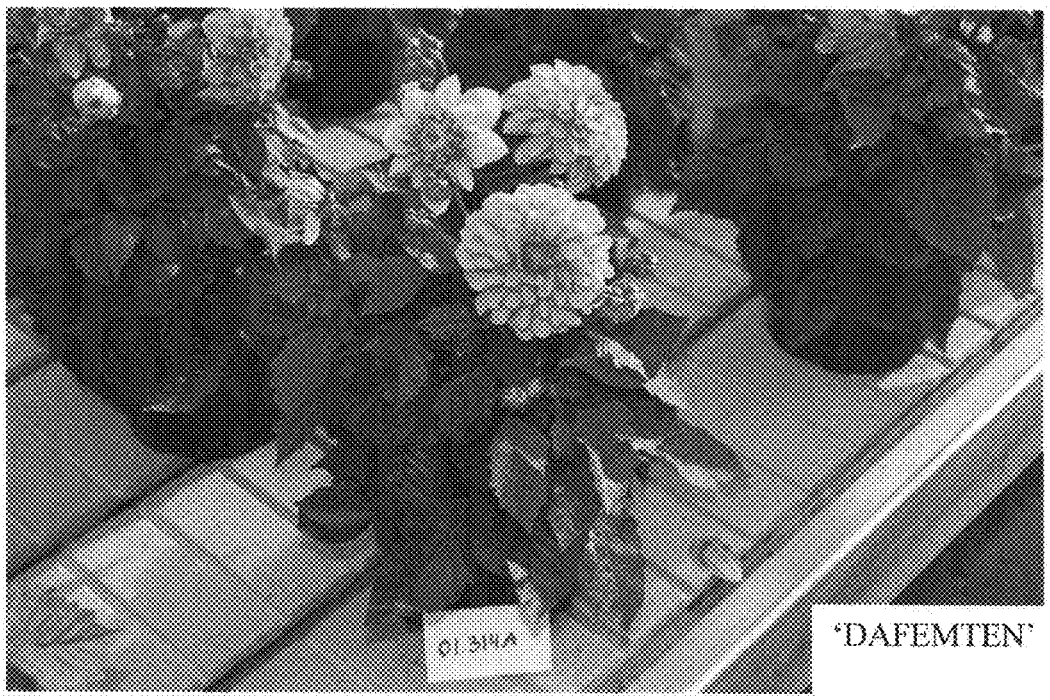

The new *Dahlia* 'DASYTTEN' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dahlia* 'DASYTTEN' as grown in a protected environment in a glass, greenhouse in Fyn, Odense, Denmark, under conditions which closely approximate those generally used in commercial practice. During propagation, conducted in a glasshouse, vegetative cuttings were planted in small propagation pots with peat as substrate, and then placed in a plastic tunnel averaging about 21° C. and received photoperiodic treatments of 18 hours. Supplementary light was given when natural light fell below 3000–4000 Lux. Rooting occurred about 12 days after planting. In third week after planting, young plants were potted in an 11 cm pot in a glasshouse maintained at 18° C. to 22° C. during the day, and at 17° C. to 19° C. during the night. Photoperiodic treatments were continued at 18 hours, and supplementary light was given when natural light fell below 3000–4000 Lux. Irrigation was done with water. The EC measured in the soil was maintained between 2.0 to 3.0. One week after potting, the first growth regulation was given: a spray with 85% daminozide, 0.2%, 40–100 ml/m$^2$. During the production time, 9 additional sprayings were given with 85% daminozide, 0.2%, 40–100 ml/m$^2$.

Color references are made to The Royal Horticultural Society Colour Chart (R.H.S.), 2001 edition, except where general colors of ordinary significance are used. Color values were taken under daylight conditions at approximately 12:00 PM and 2:00 PM in Fyn, Odense, Denmark. The age of the 'DASYTTEN' plants described is 13 weeks (including propagation time).

Classification:

*Botanical.*—*Dahlia* sp.

Parentage:

*Female or seed parent.*—*Dahlia* Cav. designated '01.1076F Toluca' (unpatented).

*Male or pollen parent.*—*Dahlia hortensis* Guillaumin designated '03.1181N' (unpatented).

Propagation:

*Type.*—Vegetative cuttings.

*Rooting description.*—Fine, fibrous; may develop tubers in late fall.

*Height of rooting structure.*—Depends on container, can grow to about 30 to 40 cm.

*Diameter of rooting structure.*—Depends on container, can grow to about 30 to 40 cm.

*Color of roots.*—Grayed-yellow, RHS 161D.

*Time to initiate roots.*—About 12 days at 21° C.

*Time to produce a rooted cutting.*—About 28 days at 21° C. during rooting phase, followed by 18° C.

*Tubers.*—Will form under short day conditions, 12 hours of darkness. Tubers may develop in late fall when planted outdoors.

Plant:

*Crop time.*—After rooting, about 7 to 9 weeks are required to produce finished flowering plants in 11–12 cm pots, provided day-length is 18 hrs.

*Plant vigor.*—Vigorous, about 4 to 6 cm per week.

*Form.*—Cylindrical, upright and slight spreading.

*Size.*—Height (from soil level to top of plant plane): About 45 to 50 cm. Spread: About 35 to 40 cm.

*Stem.*—Appearance/Shape: Circular, hollow, glabrous. Diameter: About 6 to 11 mm. Aspect: Upright to outward. Strength: Strong. Texture: Glaucous. Pubescence: Very little. Color: Brown, RHS 200A on older stems, and yellow-green, RHS 147B, on younger stems or stems exposed to less light.

*Lateral branches.*—Quantity per plant: About 4 to 6 (when pinching over 3 pair of leaves). Length (including inflorescences): About 22 to 32 cm. (including break to base of peduncle): About 12 to 14 cm. Diameter: About 6 to 11 mm. Color: Brown, RHS 200A on older branches, and yellow-green, RHS 147B, on younger stems or stems exposed to less light.

*Habit.*—Freely branching. Basal Branching: Yes. Pinching: Pinching recommended. Internode length: About 1 to 5 cm.

*Foliage.*—Type: Lower leaves: Single. Upper leaves: compound, 3–5 lobed. Quantity of leaves per lateral branch: About 8 to 10. Quantity of leaflets per compound leaf: 3 to 5. Color (leaves and leaflets): Color (mature): Upper side: Grayed-green, RHS N189A. Under side: Grayed-green, RHS 191B. Color (immature): Upper side: Green, RHS 139A. Under side: RHS, RHS 139B. Venation (leaves and leaflets): Pattern: Pinnate. Color: Upper side: Yellow green, RHS 148A. Under side: Yellow-green, RHS 146B. Simple leaves: Arrangement: Opposite, decussate. Length: About 4 to 8 cm. Width: About 2 to 8 cm. Shape: Ovate, cuspidate tip, rounded to cordate base. Margin: Dentate. Texture (both sides): Rugose. Petiole: Shape: Semi circular, with deep furrow on adaxial side. Length: About 2 to 7 cm. Diameter: About 3 to 6 mm. Color: Upper side: Brown, RHS 200B. Under side: Yellow-green, RHS 147B. Compound Leaves: Arrangement and shape: Opposite, decussate. Length: Up to 18 cm. Width: Up to 22 cm. Shape: Ovate, cuspidate tip, rounded to cordate base. Margin: Dentate. Texture (both sides): Rugose. Petiole: Shape: Semi circular. Length: About 2 to 7 cm. Diameter: About 3 to 6 mm. Color: Upper side: Brown, RHS 200B. Under side: Yellow-green, RHS 147B. Leaflets of Compound Leaf: Terminal: Quantity: 1. Length: About 11 cm. Width: About 6.5 cm. Rachis: Length: About 5 cm. Diameter: About 3 to 5 mm. Color: Upper side: Brown, RHS 200B. Under side: Yellow-green, RHS 147B. Lateral: Quantity: About 2 to 4. Length: About 12 cm. Width: About 6 cm.

Flowering description:

*Natural flowering season.*—Grown outside as a bedding plant, flowering occurs continuously during growing season from spring to autumn/ (In Denmark, from June to beginning of October). Plants can be brought to flower anytime when grown under the recommended greenhouse conditions.

*Time to first flower.*—About 7 to 9 weeks from potting of a rooted cutting.

*Longevity of individual blooms on plant.*—Depending on weather conditions, about 6 to 10 days.

*Fragrance.*—None.

Inflorescence description:

*Type.*—Capitulum (composite flower head).

*Arrangement.*—Persistent, single, composite inflorescences from leaf axils. Disk and ray florets arranged acropetally on a capitulum.

*Flowering aspect.*—Upright, slightly spreading. Young flower head/buds initially 10° to 90° turning to 0° to 30° when flower head opens.

*Quantity of flowers and buds per lateral branch.*—About 3 open capitulum and 6 buds.

*Fragrance.*—None.

*Bud.*—Quantity: Up to 6 per lateral stem (buds continue to develop when the dead composite flower heads are removed). Rate of Opening: About 2 to 5 buds per week. About 4 to 10 days for bud to progress from first color to fully opened inflorescence. Shape: Globular. Length (when color shows): About 1.2 to 1.5 cm. Diameter (when color shows): About 1.5 to 2.0 cm. Texture: Glabrous, shining. Color: Yellow-green, RHS 144A.

*Peduncle.*—Length: About 10 to 18 cm. Diameter: About 3 to 4 mm. Strength: Moderately strong. Aspect (angle to vertical): First flower: About 0° to 10°. Second flower: About 20° to 30°. Texture: Glabrous. Color: Mature: Brown, RHS 200B; Immature: Yellow-green, RHS 146B.

*Inflorescence.*—Inflorescence depth (height): About 5 to 6 cm. Inflorescence diameter: About 10 cm. Disk diameter: About 8.5 cm. Receptacle diameter: About 10 mm. Receptacle height: About 4 to 6 mm.

*Ray florets.*—Arrangement: Imbricate, in about 9 to 14 whorls of ray florets, each with 9 to 11 florets to equal a total of about 110–140 ray florets per capitulum, depending on light and temperature conditions. Overall shape: Obovate, involute with a rounded tip. Apex shape: Obtuse. Base shape: Acuminate, fused to form tube. Length: About 30 to 40 mm. Diameter (width): About 20 to 28 mm. Margin: Entire. Texture: Upper and under surfaces: Glabrous. Orientation: Initially 10° from vertical, with development, to 70° from vertical. Color: Development and tones of color for florets may change slightly depending on light and temperature conditions. When opening: Upper surface: Near base, green-yellow, RHS 1A, transitioning to yellow-orange, RHS 23A, at tip. Under surface: Near base, green-yellow, RHS 1A, transitioning to grayed-orange, RHS N163C, at tip. When fully opened: Upper surface: Near base, green-yellow, RHS 1B, transitioning to yellow-orange, RHS 17C, at tip. Under surface: Near base, green-yellow, RHS 1B, transitioning to yellow-orange, RHS 22A, at tip.

*Disk florets.*—Arrangement: Massed at center of capitulum, about 40–70 disk florets per capitulum, which are yellow-orange RHS 14A in color. Appearance: Tubular to single, fused corolla. Overall shape: Tubular. Apex shape: Star with 5 triangular tips. Base shape: Fused to tube. Length: About 8 to 9 mm. Diameter: About 1 to 1.5 mm. Margin: Entire. Texture (both surfaces): Glabrous, translucent. Color: Transparent, yellow-orange, RHS 14A.

*Phyllaries.*—Quantity: One subtending each floret. About 110 to 140 phyllaries per capitulum. Overall shape: Thin translucent, papery. Phyllaries, arranged acropetally on the capitulum. Overall shape: Rounded. Apex shape: Acute with rounded tip. Base shape: Fused. Length: About 6 to 10 mm. Width: About 4 to 6 mm. Margin: Entire. Color: Mature: Yellow-green, RHS 151B. Immature: Primarily yellow-green, RHS 151D, to green, RHS 144A, near base.

*Bracts.*—Quantity: About 5 to 7. Appearance and arrangement: Reflexed, involucral bracts. Overall shape: Subulate. Apex shape: Acute. Base shape: Sessile. Length: About 10 to 18 mm. Width: About 6 to 8 mm. Margin: Entire. Texture (both sides): Glabrous. Color: Mature: Upper side: Green, RHS 137A. Under side: Primarily, yellow-green, RHS 151D, to yellow-green, RHS 144A, near base. Immature: Upper side: Green, RHS 137A. Under side: Green, RHS 137A.

Reproductive organs:

Androecium:

*Stamen.*—Number: 5, fused into synandrous tube around style. Disk florets fertile, ray florets sterile. Length: About 8 to 10 mm.

*Anther.*—Shape: Tubular. Length: About 5 to 6 mm. Color: Yellow-orange, RHS 20A.

*Pollen.*—Amount: Scarce. Color: Yellow-orange, RHS 23A.

Gynoecium:

*Pistil.*—Quantity: One per disk floret. Length: About 8 to 9 mm.

*Stigma.*—Shape: Bifurcate. Length: About 1 to 2 mm. Color: Yellow-orange, RHS 20A.

*Style.*—Length: About 4 to 7 mm. Color: Yellow-orange, RHS 20D.

*Ovary.*—Shape: Globular Diameter: About 1 mm. Color: Yellow-green, RHS 151D.

Seed/fruit: None observed.

Disease/pest resistance: Resistance to pathogens and pests common to *Dahlia* has not been observed.

Disease/pest susceptibility: Susceptibility to pathogens and pests common to *Dahlia* has not been observed.

Temperature tolerance: Tolerant to a low temperature of about 2° C. (but flowering ceases at constant temperature below 12° C.) and tolerant to a high temperature of about 35° C. Optimum flowering occurs only between 12° C. and 30° C. High temperatures might reduce flowering.

Growth regulators: Daminozide (85% water soluble dry concentrate formulation).

I claim:

1. A new and distinct cultivar of *Dahlia* plant named 'DASYTTEN', as described and illustrated herein.

* * * * *

'DASYTTEN'

'DAFEMTEN'